United States Patent
Choi et al.

(10) Patent No.: US 10,408,800 B2
(45) Date of Patent: Sep. 10, 2019

(54) REAL-TIME AUTOMATIC ANALYSIS DEVICE FOR ORGANIC CONTAMINANT IN WATER

(71) Applicant: REPUBLIC OF KOREA (MINISTRY OF ENVIRONMENT, NATIONAL INSTITUTE OF ENVIRONMENTAL RESEARCH), Incheon (KR)

(72) Inventors: In-Cheol Choi, Namyangju (KR);
Hyen-Mi Chung, Seoul (KR);
Ju-Hyun Park, Incheon (KR);
Oh-Sang Kwon, Goyang (KR);
Yu-Jeong Huh, Incheon (KR);
Kyung-Hee An, Incheon (KR)

(73) Assignee: REPUBLIC OF KOREA (MINISTRY OFENVIRONMENT, NATIONAL INSTITUTE OF ENVIRONMENTAL RESEARCH), Incheon (KR)

( * ) Notice: Subject to any disclaimer, the term of this patent is extended or adjusted under 35 U.S.C. 154(b) by 224 days.

(21) Appl. No.: 15/326,671

(22) PCT Filed: Sep. 23, 2015

(86) PCT No.: PCT/KR2015/010024
§ 371 (c)(1),
(2) Date: Jan. 17, 2017

(87) PCT Pub. No.: WO2016/052914
PCT Pub. Date: Apr. 7, 2016

(65) Prior Publication Data
US 2017/0219537 A1 Aug. 3, 2017

(30) Foreign Application Priority Data
Sep. 30, 2014 (KR) .......................... 10-2014-0131465

(51) Int. Cl.
*G01N 30/06* (2006.01)
*G01N 30/24* (2006.01)
(Continued)

(52) U.S. Cl.
CPC ............... *G01N 30/06* (2013.01); *G01N 1/10* (2013.01); *G01N 30/24* (2013.01);
(Continued)

(58) Field of Classification Search
CPC ....... G01N 2001/002; G01N 2030/009; G01N 2030/884; G01N 30/06; G01N 30/7206; G01N 33/1826; G01N 30/88; E02D 1/06
(Continued)

(56) References Cited

U.S. PATENT DOCUMENTS

| 6,685,828 B2 * | 2/2004 | Berger | B01D 11/0203 210/198.2 |
| 2002/0121148 A1 * | 9/2002 | Shinozaki | G01N 1/22 73/863.33 |
| 2014/0377878 A1 * | 12/2014 | Beecroft | B01L 9/06 436/161 |

FOREIGN PATENT DOCUMENTS

| JP | 2004-117058 | 4/2004 |
| KR | 10-2001-0014629 | 2/2001 |

(Continued)

*Primary Examiner* — Eric S. McCall
*Assistant Examiner* — Timothy P Graves
(74) *Attorney, Agent, or Firm* — Lex IP Meister, PLLC

(57) ABSTRACT

The present invention relates to a real-time automatic analysis device for an organic contaminant in water, the device having: an analysis apparatus comprising a solid phase micro-extraction device and a gas chromatography/mass spectrometry analysis device that have been traditionally used; a heating block; a sample bottle; a discharge unit; and a control unit. While using an analysis apparatus, being traditionally used, as it is, the real-time automatic analysis device for an organic contaminant in water accurately and (Continued)

quickly identifies a point of generation of a high-concentration organic contaminant by supplying a sample consecutively and in real time, takes follow-up measures, and easily performs a sensory analysis as well as a chemical analysis.

3 Claims, 7 Drawing Sheets

(51) Int. Cl.
 *G01N 30/72* (2006.01)
 *G01N 33/18* (2006.01)
 *G01N 1/10* (2006.01)
 G01N 1/18 (2006.01)
 G01N 30/88 (2006.01)
(52) U.S. Cl.
 CPC ..... *G01N 30/7206* (2013.01); *G01N 33/1826* (2013.01); *G01N 1/18* (2013.01); *G01N 30/88* (2013.01)
(58) Field of Classification Search
 USPC .................................................. 73/23.35–41
 See application file for complete search history.

(56) References Cited

FOREIGN PATENT DOCUMENTS

| KR | 10-0562478 | 3/2006 |
| KR | 10-2008-0099032 | 11/2008 |
| KR | 10-1267987 | 5/2013 |

\* cited by examiner

REAL-TIME AUTOMATIC ANALYSIS DEVICE FOR ORGANIC CONTAMINANT IN WATER

TECHNICAL FIELD

The present invention relates to a real-time automatic analysis system for organic contaminants in water that is capable of rapidly and accurately detecting a time point when high concentrations of harmful organic contaminants are generated from the samples taken in real time and continuously, even while utilizing an existing analyzer, thereby quickly taking appropriate measures in a water purifying plant.

BACKGROUND ART

Owing to industrialization and urbanization, environmental pollution has emerged as a social issue for a long time, and accordingly, the control of water quality such as the protection of water supply sources and the management and regulation of pollutant discharge facilities becomes strict systematically on a national level. It is the basis of the control is to quickly and accurately measure the contaminants in water. Through rapid water quality measurement for raw water, purified water, and running water related to drinking water, an appropriate water purification process is applied, and therefore, the water quality measurement is very important in view of safety.

Organic contaminants, which are managed by a water supply system, include tens of substances such as volatile organic compounds, agricultural chemicals, disinfection by-products, taste and odor substances and so on. Because such organic contaminants give harmful effects on people's health or cause an aesthetic problem on the water containing them, they have a direct influence on the water quality, and accordingly, complete management for each substance of the organic contaminants should be required. Among them, the taste and odor substances (geosmin and 2-MIB) are increased in the concentration and frequency introduced in a water purifying plant due to the increment of algal blooms in a water supply source caused recently by climate changes like water temperature increases and rainfall pattern changes, and so as to rapidly treat the taste and odor substances before they are introduced into a water distribution network, accordingly, a water purifying material like powdered activated carbon has to be applied to the water purifying plant to allow the purified water to have a value less than an odor threshold value, thereby avoiding the complaints of consumers. Therefore, more careful management for the taste and odor substances should be needed.

The taste and odor substances are normally analyzed manually, less than once a day, in a water purifying plant, and if they are generated in high concentrations, they are analyzed twice a day. However, it is not easy to cope with rapid water purification process through the manual analysis of the water qualities varied from hour to hour. Further, the volatile organic compounds and agricultural chemicals are generated in small quantities on emergency situations like leakage accidents of chemical factories in a water supply system and rollover accidents of tank lorries carrying chemicals, but the disinfection by-products generated in the water purification process have to be monitored in real time. In this case, also, they are measured manually, so that it is hard to rapidly cope with them through rapid detection.

So as to solve the above-mentioned problems, endeavors for monitoring water quality in real time have been tried in conventional practices.

For example, various technologies for monitoring water quality in real time have been suggested in Korean Patent No. 10-0901779 (Jun. 2, 2009) entitled 'internet-based monitoring and control system for measuring water quality', Korean Patent No. 10-0522764 (Sep. 12, 2005) entitled 'real-time water quality monitoring device and method for controlling the same', Korean Patent No. 10-1406884 (Jun. 5, 2014) entitled 'multi-wavelength analysis-based on-line water quality measuring system for real-time detection of organic contaminants in water', and Korean Patent No. 10-1253251 (Apr. 4, 2013) entitled 'real-time taste and odor substance monitoring and control device and method for water purification'.

DISCLOSURE

Technical Problem

By the way, most of the above-mentioned conventional technologies just measure basic water quality parameters (water temperature, pH, turbidity, residual chlorine electrical conductivity, etc.) or total organic compound indexes (TOC, COD, etc.), and even if some of them measure special organic contaminants like volatile organic compounds and taste and odor substances, they make use of different analyzers from the existing analyzer or combine various expensive equipment with one another, thereby decreasing the accuracy, reliability, and economical effects in the measurement and making it hard to operate and manage.

As mentioned above, further, the organic contaminants in water like the taste and odor substances should be analyzed in real time. However, the conventional technologies for the analysis of the organic contaminants in water like the taste and odor substances suggest separate expensive equipment combinations, so that they are not economical and they become complicated in operation and management. Recently, an analyzer having a solid-phase microextraction unit and a gas chromatography/mass spectrometer has been widely used as the equipment for analyzing the organic contaminants in water, but since they do not utilize the typical analyzer, new equipment should be installed inconveniently.

Technical Solution

It is an object of the present invention to provide a real-time automatic analysis system for organic contaminants in water that achieves the automation in all measuring processes of each organic pollutant in water, while using an existing analyzer used for manual analysis, thereby in real time utilizing the measured results for water quality control, and further analyzes given organic substances like taste and odor substances, volatile organic compounds, agricultural chemicals, and disinfection by-products in real time to allow the organic substances to be measurable to concentrations (to a given number of ng/L level in case of the taste and odor substances) to be controllable, thereby increasing the reliability of the measured values and the economical effects and providing easiness in the maintenance, installation and manipulation.

Advantageous Effects

According to the present invention, the real-time automatic analysis system for organic contaminants in water can additionally mount, the sample bottles specially designed, the heating block capable of conducting temperature control and agitation, the sample supply and discharge unit, the drainage line, and the sample supply quantity control line, and the passage change unit capable of changing the flows of the samples according to programs, on the existing analyzer, and thus drive them unitarily with the existing analyzer, so that the organic contaminants in water like the taste and odor substances in water can be analyzed in real time and continuously, thereby rapidly detecting the time point when high concentrations of organic contaminants are generated and thus taking appropriate measures.

Further, the real-time automatic analysis system for organic contaminants in water according to the present invention can obtain a desired level of measurement sensitivity for the organic contaminants through the appropriate capacities of the sample bottles and the heating means and agitator of the heating block, without having any expensive and complicated equipment and any separate chemicals, can be simply disposed on the existing analyzer, can be easy in operation and maintenance thereof, and can be very economical and practical.

Furthermore, the real-time automatic analysis system for organic contaminants in water according to the present invention can seat the plurality of sample bottles in the heating block, thereby conducting the water quality measurement at various positions as the objects to be analyzed.

Figure 1:
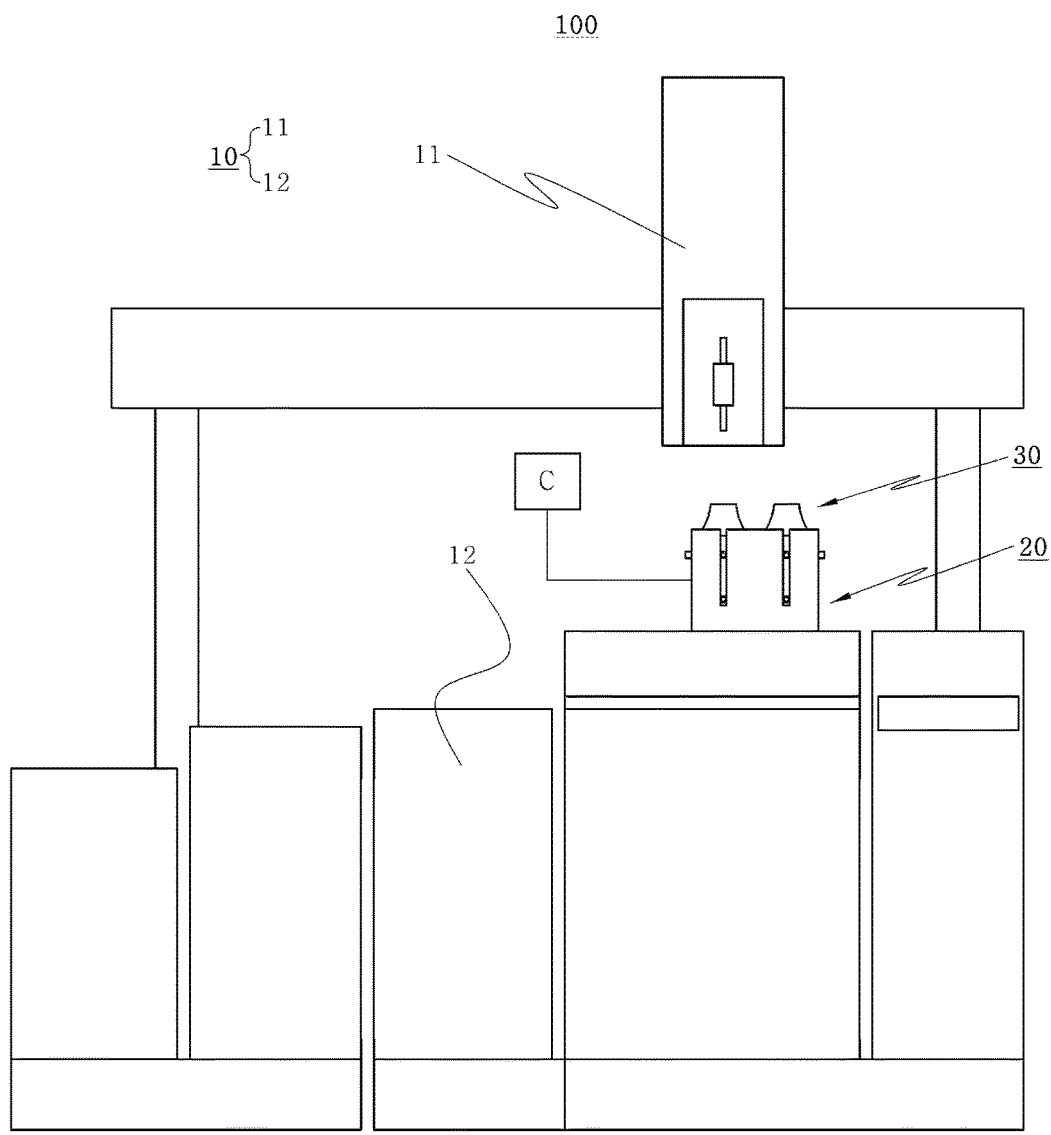
FIG. 1 is a side view showing a real-time automatic analysis system for organic contaminants in water according to the present invention.

[Explanation on Reference Numerals in the Drawing]

C: controller
10: analyzer
11: solid-phase microextraction device
12: gas chromatography/mass spectrometry device
20: heating block
21: sample bottle seating recess    22: heating means
23: temperature sensor    24: agitator
30: sample bottle
31: accommodation portion    32: sample supply portion
33: sample discharge portion
34: sample supply quantity control portion

[Explanation on Reference Numerals in the Drawing]

40: sample supply and discharge unit
42: sample supply line
42a: sample supply control valve
42b: pump    43: sample discharge line
43a: sample discharge control valve
50: drainage line
51: drainage control valve
60: sample supply quantity control line
61: sample supply quantity control valve
100: real-time automatic analysis system for organic contaminants in water

MODE FOR INVENTION

Hereinafter, an explanation on a real-time automatic analysis system for organic contaminants in water according to the present invention will be in detail given with reference to the attached drawings.

First, as shown in FIG. 1, a real-time automatic analysis system 100 for organic contaminants in water according to the present invention includes an analyzer 10 having a solid-phase microextraction (SPME) device 11 for extracting a very small quantity of a sample and a gas chromatography/mass spectrometry device 12 for receiving the sample extracted from the solid-phase microextraction device 11 to conduct qualitative and quantitative analysis for the sample containing the organic contaminants.

Even if not shown in detail in the figure, the solid-phase microextraction device 11 is configured wherein a fiber capable of absorbing the sample is inserted and drawn into/from a needle of a syringe for sampling (concentration/extraction), and after the sample to be analyzed has been taken, accordingly, the needle of the syringe is put into a sample introduction portion (not shown) formed on the gas chromatography/mass spectrometry device 12 to allow the sample to be analyzed qualitatively and quantitatively.

Particularly, the gas chromatography of the gas chromatography/mass spectrometry device 12 serves to separate the substances mixed in the sample, as well known, and if the mass spectrometer is used as the detector of the gas chromatography, the molecular mass of the separated substances is accurately obtained with a value of up to 5 digits after the point, thereby conducting the qualitative and quantitative analysis for the mixed substances of the sample.

So as to analyze the sample, desirably, the solid-phase microextraction device 11 is generally attached to the top side of the gas chromatography/mass spectrometry device 12.

Next, as shown in FIGS. 1 to 4, the real-time automatic analysis system 100 for organic contaminants in water according to the present invention includes a heating block 20 disposed between the solid-phase microextraction device 11 and the gas chromatography/mass spectrometry device 12, in more detail, on top of the gas chromatography/mass spectrometry device 12, and having a plurality of sample bottle seating recesses 21 formed at the inside thereof, heating means 22 for raising the whole temperature, and a temperature sensor 23.

In this case, the sample bottle seating recesses 21 are spaced apart from each other by a given distance, and the heating block 20 further includes a magnetic or vibration agitator 24 disposed therein.

Next, as shown in FIGS. 1 to 4, the real-time automatic analysis system 100 for organic contaminants in water according to the present invention includes a plurality of sample bottles 30 seated in the sample bottle seating recesses 21 formed in the heating block 20, and each sample bottle 30 has an accommodation portion 31 formed therein to accommodate the sample for water quality measurement therein, so that the sample accommodated in the accommodation portion 31 is absorbed to the solid-phase microextraction device 11 of the analyzer 10.

In this case, a capacity of the accommodation portion 31 of each sample bottle 30 is desirably in a range of 100 to 150 ml, which is of course not limited particularly thereto.

Of course, each sample bottle 30 has a stopper (not shown) disposed on top thereof so as to pass the needle of the syringe therethrough, while sealing the sample bottle 30.

Further, each sample bottle 30 has a sample supply portion 32 for supplying the sample to the accommodation portion 31 and a sample discharge portion 33 for discharging the sample accommodated in the accommodation portion 31 after the sample has been taken (concentrated/extracted) by the analyzer 10 for the analysis of the sample to the outside.

In this case, desirably, the sample supply portion 32 is formed on the upper end of the side periphery of the sample bottle 30, and the sample discharge portion 33 is on the lower end of the side periphery of the sample bottle 30 so as to easily discharge the sample to the outside, which are of course not limited particularly thereto.

Next, the real-time automatic analysis system 100 for organic contaminants in water according to the present invention includes a sample supply and discharge unit 40 connected to each sample bottle 30 to supply and discharge the sample to and from the sample bottle 30.

Figure 2:
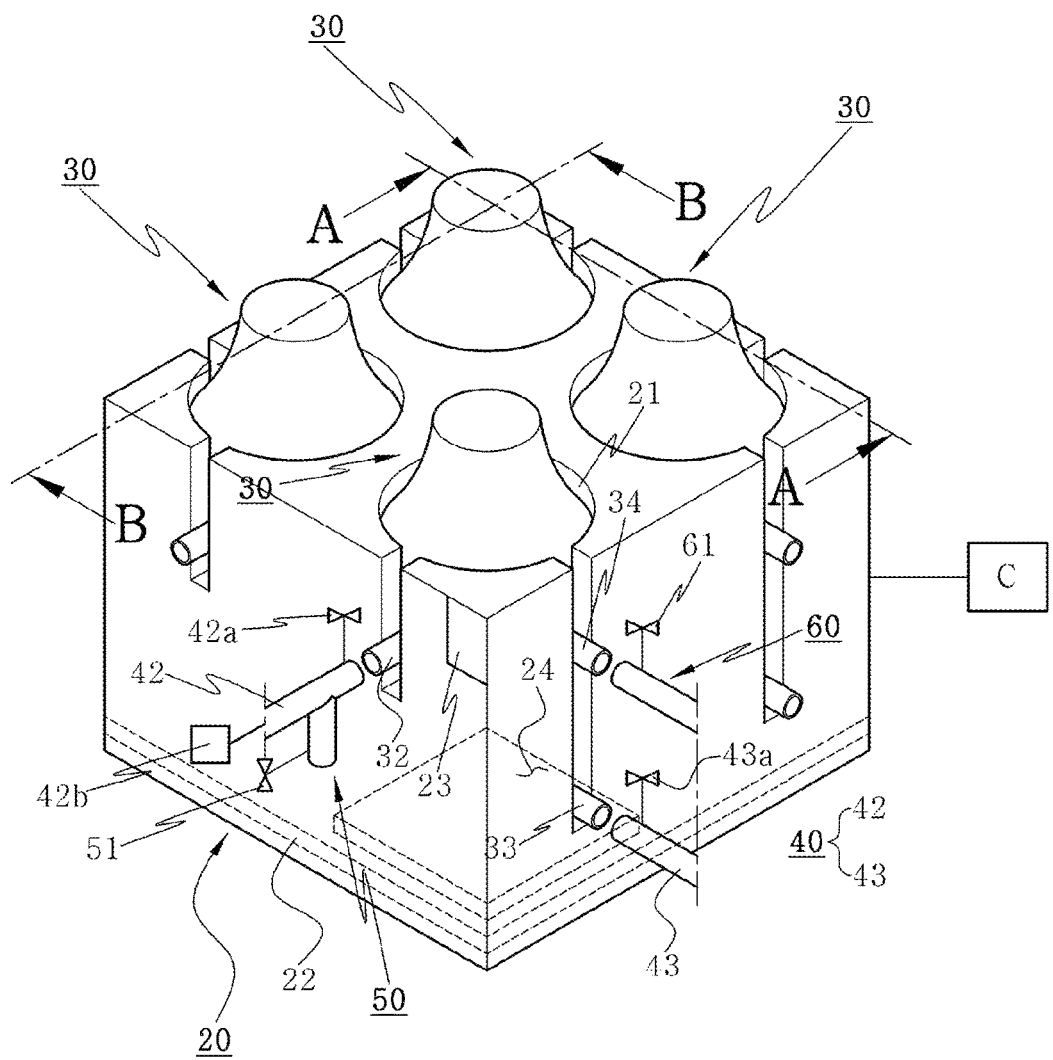
FIG. 2 is a perspective view showing a coupling relation between a heating block and sample bottles in the real-time automatic analysis system according to the present invention.
Figure 3:
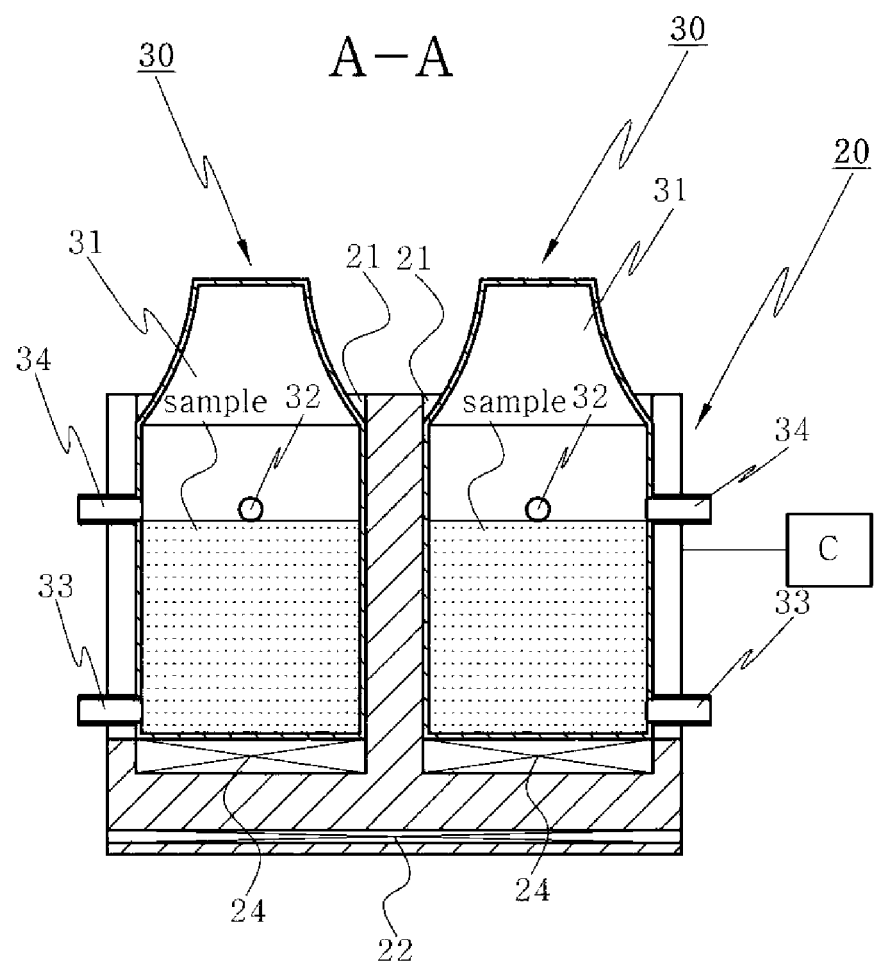
FIG. 3 is a sectional view taken along the line A-A of FIG. 2.
Figure 4:
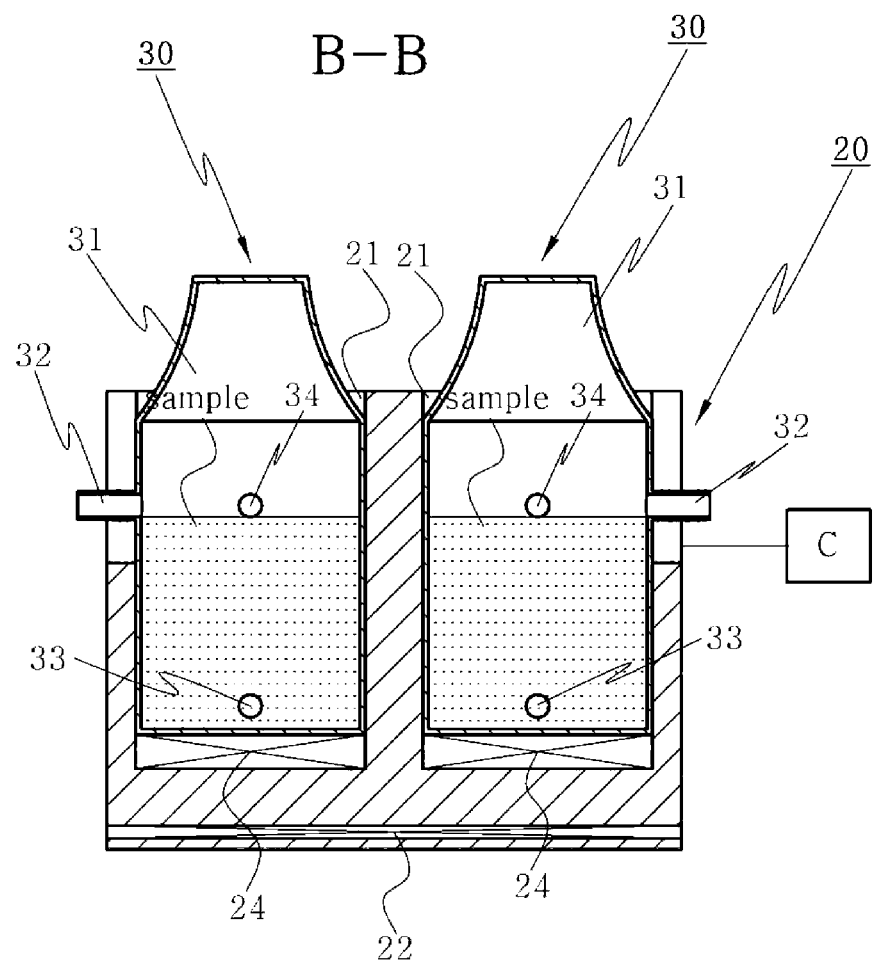
FIG. 4 is a sectional view taken along the line B-B of FIG. 2.

As shown in FIG. 2, the sample supply and discharge unit 40 includes a sample supply line 42 connected to the sample supply portion 32 of each sample bottle 30 and having a sample supply control valve 42a disposed thereon to conduct sample supply and sample supply cutoff.

That is, one end of the sample supply line 42 is connected to the sample bottle 30 and the other end thereof is connected to a line along which a medium to be analyzed, that is, an object to be measured in water quality, such as raw water (rivers, lakes, etc.), processed water in a water purifying plant, purified water, and the like, flows, so that the sample can be supplied in real time to the accommodation portion 31 of the sample bottle 30.

In this case, the sample supply and discharge unit 40 further includes a pump 42b disposed on a portion of the sample supply line 42 connected to a position at which the water quality measurement for the sample is conducted by the analyzer 10, so that the fluid (sample) is movable. In addition, a washing line (not shown) for supplying washing water to the sample bottle 30 to wash the interior of the sample bottle 30 is connected to the end portion of the sample supply line 42. Otherwise, a portion from which washing water is supplied is connected to the end portion of the sample supply line 42, so that the washing water is supplied to the sample bottle 30.

On the other hand, a drainage line 50 is connected to the sample supply line 42 so as to always supply a new sample to the sample supply line 42.

The drainage line 50 is branched from the sample supply line 42 and is desirably formed between the position at which water quality measurement is conducted and the sample supply control valve 42a of the sample supply line 42, more desirably formed just before the sample supply control valve 42a.

According to the present invention, on the other hand, the real-time automatic analysis system 100 for organic contaminants in water includes components for filling the sample in each sample bottle 30 by a given amount so that the quantitative analysis for the sample can be achieved.

In more detail, each sample bottle 30 has a sample supply quantity control portion 34 for accommodating only a given quantity of sample in the accommodation portion 31, and the sample supply quantity control portion 34 is formed on the side periphery of each sample bottle 30 at an accurate height up to which the sample is filled in the accommodation portion 31, so that only the given quantity of sample can be accommodated in the accommodation portion 31.

Further, a sample supply quantity control line 60 is connected to the sample supply quantity control portion 34 of each sample bottle 30 and has a sample supply quantity control valve 61 disposed thereon.

In this case, the above-mentioned valves are electronically controllable like a solenoid valve in such a manner as to be open and closed by the control of a controller C.

Under the above-mentioned configuration, a preferred embodiment of the real-time automatic analysis system 100 for organic contaminants in water according to the present invention will be explained below.

First, the real-time automatic analysis system 100 for organic contaminants in water according to the present invention automatically analyzes the organic contaminants in water in real time, while still using the existing analyzer 10, and accordingly, the real-time automatic analysis system 100 according to the present invention is installed in a site or laboratory within a given region for water quality measurement of analysis water such as purified water, raw water, and processed water produced in a water purifying facility like a water purifying plant.

After that, the analysis water is in real time supplied to the sample supply line 42 of the sample supply and discharge unit 40 connected to the sample supply portion 32 of each sample bottle 30.

Figure 5:
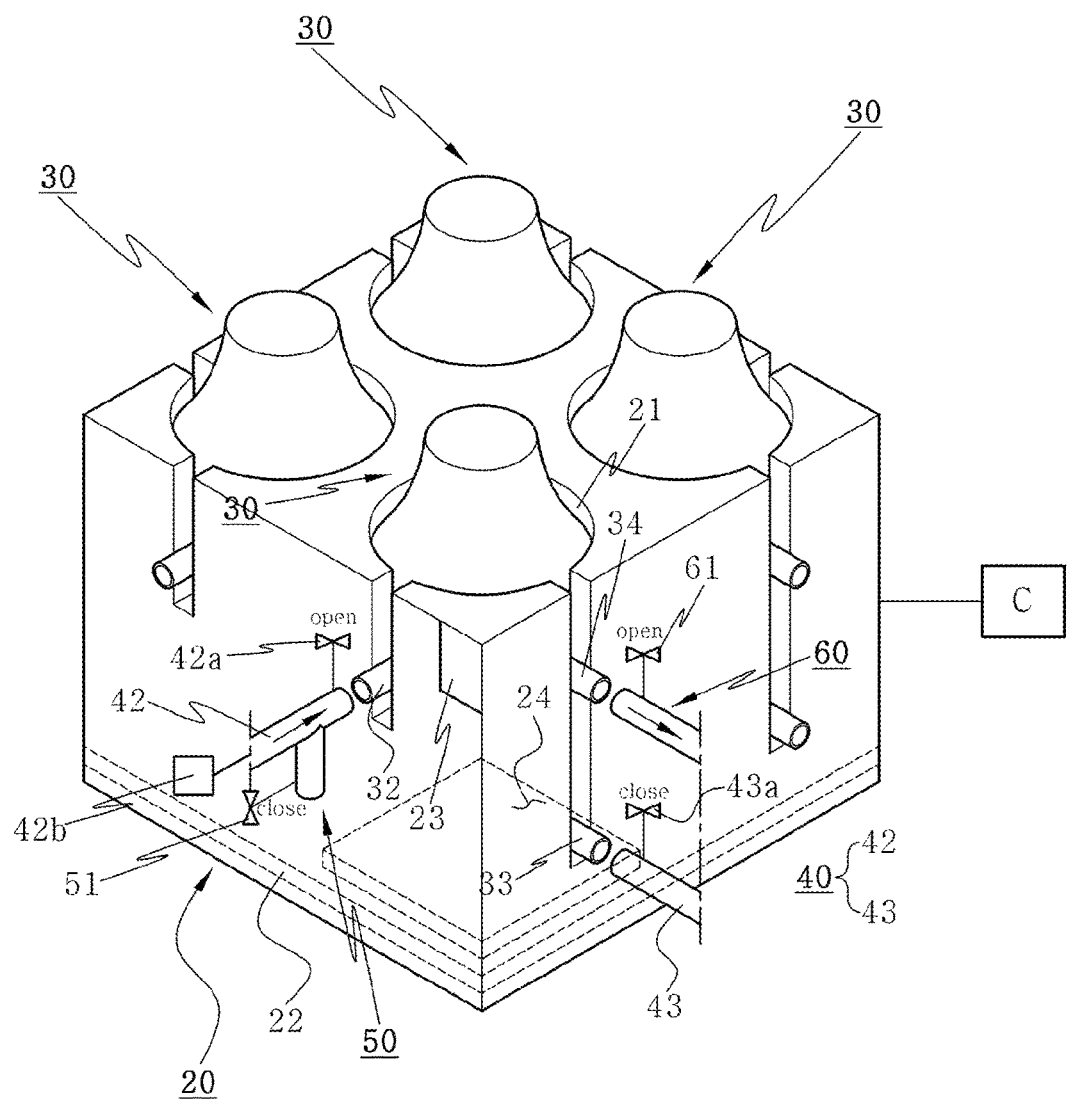
FIG. 5 is a perspective view showing the state where a sample is supplied to a sample bottle in the real-time automatic analysis system according to the present invention.

As shown in FIG. 5, a process for supplying the analysis water to each sample bottle 30 through the sample supply line is carried out as the sample supply control valve 42a disposed on the sample supply line 42 is open by the control of the controller C, and on the other hand, as the sample discharge control valve 43a of the sample discharge line 43 of the sample supply and discharge unit 40 connected to the sample discharge portion 33 of each sample bottle 30 and the drainage control valve 51 of the drainage line 50 connected to the sample supply line 42 are closed by the control of the controller C, the sample as the analysis water is filled in the accommodation portion 31 of each sample bottle 30.

In this case, the sample supplied from the sample supply line 42 is movable by means of the pump 42b or a pressure of purified or raw water.

If the quantity of sample filled in the sample bottle 30 reaches a given level, that is, a position at which the sample supply quantity control portion 34 is formed on the sample bottle 30, the quantity of sample overfilled in the sample bottle 30 is discharged to the outside through the sample supply quantity control line 60 connected to the sample supply quantity control portion 34, so that only the given quantity of sample is filled in the accommodation portion 31 of the sample bottle 30.

Figure 6:
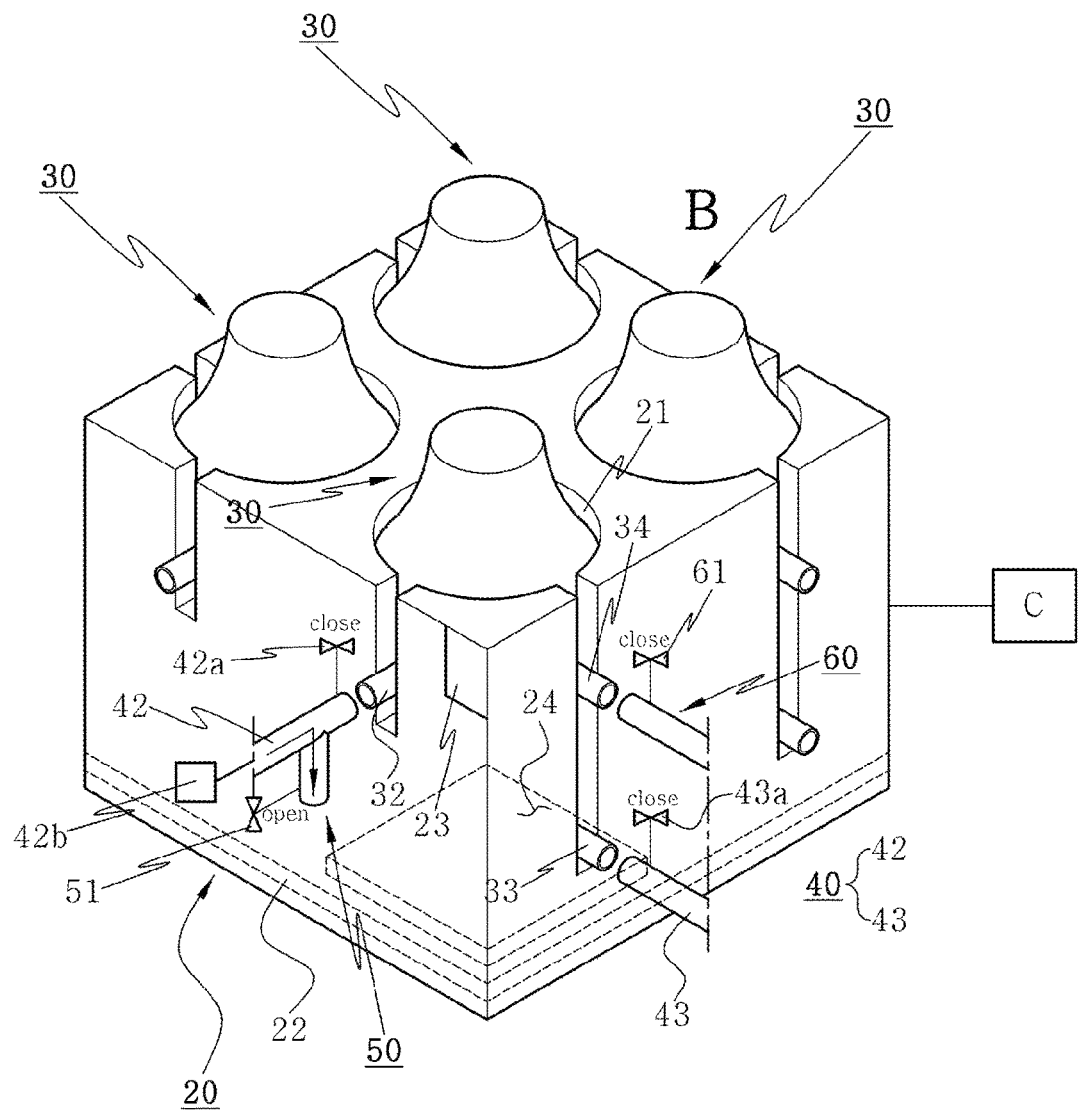
FIG. 6 is a perspective view showing the state where the sample of the sample bottle is taken (concentrated/extracted) through an analyzer of the real-time automatic analysis system according to the present invention.

So as to allow the sampling (concentration/extraction) and analysis operations to be carried out through the analyzer 10, as shown in FIG. 6, after the given quantity of sample has been filled in the accommodation portion 31 of the sample bottle 30, the sample supply control valve 42a disposed on the sample supply line 42 and the sample supply quantity control valve 61 disposed on the sample supply quantity control line 60 are closed by the control of the controller C to allow the accommodation portion 31 of the sample bottle 30 to be blocked from the outside, and as the drainage control valve 51 of the drainage line 50 is open by the control of the controller C, on the other hand, the sample supplied continuously from the sample supply line 42 is discharged through the drainage line 50.

In this case, the drainage line 50 serves to allow the sample existing in the sample supply line 42 to remain with only the quantity supplied in real time.

As mentioned above, the real-time automatic analysis system according to the present invention analyzes the sample supplied in real time to rapidly detect a time point when the organic contaminants are generated from the sample, and in this case, the formation of the drainage line 50 permits the sample existing in the sample supply line 42 to be supplied in real time, thereby enabling the real-time analysis for the sample.

Next, the needle of the solid-phase microextraction device 11 is located in a headspace of the sample bottle 30 to conduct the concentration/extraction of the sample.

So as to allow the organic contaminants of the sample in the accommodation portion 31 of the sample bottle 30 to be moved well to the headspace of the sample bottle 30, on the other hand, the heating block 20 in which the sample bottle is accommodated raises the temperature of the sample bottle 30 to a good temperature (which is controlled according to analysis parameters) for analysis, and operates the agitator 24 if necessary.

After that, the solid-phase microextraction device 11 is operated to absorb the sample of the sample bottle 30 and thus to introduce the absorbed sample into the gas chromatography/mass spectrometry device 12, thereby conducting the analysis for the sample.

Even while the sample analysis is being conducted through the analyzer 10, of course, the samples are supplied continuously to other sample bottles 30 through the above-mentioned components, so that if the analysis of the corresponding sample is finished through the analyzer 10, the sample of another sample bottle 30 can be continuously analyzed.

Figure 7:
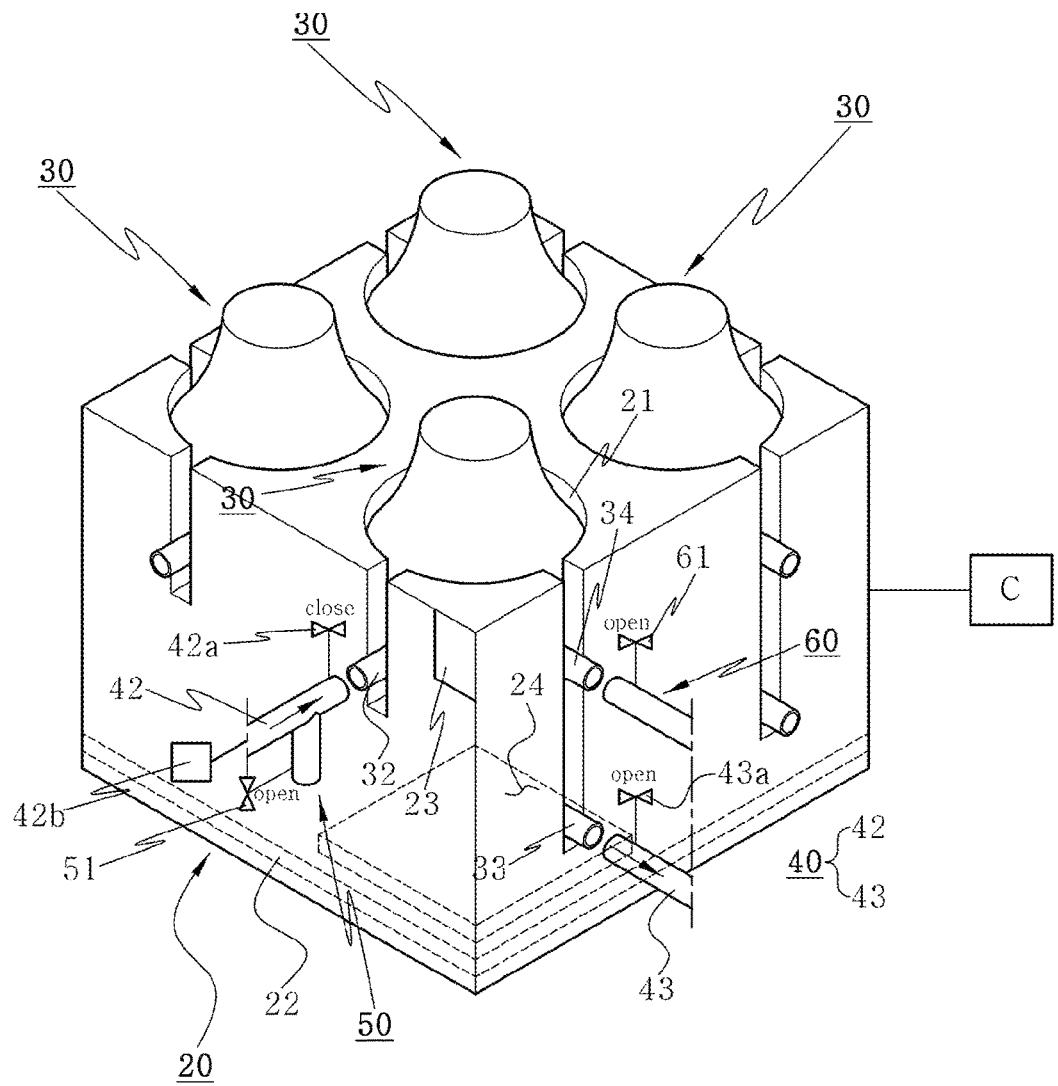
FIG. 7 is a perspective view showing the state where the sample is discharged from the sample bottle in the real-time automatic analysis system according to the present invention.

As the sample discharge control valve 43a of the sample discharge line 43 of the sample supply and discharge unit 40 connected to the sample discharge portion 33 of the sample bottle 30 and the sample supply quantity control valve 61 disposed on the sample supply quantity control line 60 are open, on the other hand, the sample remaining in the sample bottle 30 from which the sample is taken through the analyzer 10 is discharged to the outside, as shown in FIG. 7, and while the sample is being supplied again from the sample supply line 42, next, the sample discharge control valve 43a is closed after the sample remaining initially in the accommodation portion 31 of the sample bottle 30 has been discharged through the sample discharge line 43. In this state, the sample supply quantity control valve 61 of the sample supply quantity control line 60 is closed to repeatedly conduct the sample accommodation and analysis.

At this time, the sample supplied from the sample supply line 42 of the sample supply and discharge unit 40 is supplied in real time, so that the real-time sampling and the sample analysis of the analyzer 10 can be continuously conducted to rapidly detect a time point when high concentrations of organic contaminants are generated and to achieve continuous analysis for the samples.

According to the present invention, on the other hand, the plurality of sample bottles 30 is disposed on the heating block 20, and in this case, the samples are taken from only a place. However, the sample supply and discharge unit 40 connected to one sample bottle 30 is disposed on purified water, and the sample supply and discharge unit 40 connected to another sample bottle 30 is disposed on raw water, so that the samples are taken from various places and analyzed at a time through the analyzer 10.

According to the present invention, further, the capacity of each sample bottle 30 is desirably in a range of about 100 to 150 ml, so that sufficient quantities of organic contaminants for analysis can be contained in each sample bottle 300. On the other hand, the temperatures of the sample bottles 30 are kept warm through the heating means 22 and the temperature sensor 23 of the heating block 20, and further, the collection (pre-processing of concentration/extraction) of the samples is effectively carried out through the agitator 24 of the heating block 20, so that upon the analysis of the samples through the analyzer 10, analysis sensitivity can be enough obtained, without having the injection of any separate reaction chemicals.

If the analysis of the samples is the process for automatically analyzing the taste and odor substances of the samples, particularly, sensory analysis can be further carried out to allow a worker to smell the samples, in addition to the chemical analysis through the analyzer 10.

If a temperature of the sample is low, the level of analysis sensitivity through the sense of smell becomes decreased. So as to conduct the sensory analysis, accordingly, the temperature of the sample is first raised, and then, a large number of preparation processes are needed. According to the present invention, however, the sensory analysis is just carried out upon the analysis of the samples through the introduction of the heating block 20, thereby enabling the continuous analysis to be carried out in real time and further shortening the time for the analysis.

As described above, the real-time automatic analysis system for organic contaminants in water according to the present invention can mount separate components on the existing analyzer, while utilizing the existing analyzer, and can rapidly and accurately detect the time point when high concentrations of organic contaminants are generated from the samples through the supply of the samples in real time and continuously, so that the analysis system can be applied simply to the existing analyzer 10, without any additional or new equipment, thereby having very useful economical effects.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A real-time automatic analysis system for organic contaminants in water, the analysis system comprising:
   an analyzer (10) having a solid-phase microextraction device (11) for extracting a very small quantity of a sample and a gas chromatography/mass spectrometry device (12) for receiving the sample extracted from the solid-phase microextraction device (11) to conduct qualitative and quantitative analysis for the sample containing the organic contaminants;
   a heating block (20) disposed under the solid-phase microextraction device (11) of the analyzer (10) and having a plurality of sample bottle seating recesses (21), heating means (22), and a temperature sensor (23) formed at the inside thereof;

a plurality of sample bottles (30) seated in the sample bottle seating recesses (21) of the heating block (20), each sample bottle (30) having an accommodation portion (31) formed therein to accommodate the sample therein, a sample supply portion (32) for supplying the sample in real time to the accommodation portion (31), and a sample discharge portion (33) for discharging the sample accommodated in the accommodation portion (31) outside each sample bottle;

a sample supply and discharge unit (40) having distinct sample supply lines (42) connected to the sample supply portion (32) of each sample bottle (30) to conduct the supply of the sample, each sample supply line (42) having a distinct sample supply control valve (42*a*) disposed thereon, and a distinct sample discharge line (43) connected to each sample discharge portion (33) of each sample bottle 1301 to conduct the discharge of the sample from the accommodation portion (31), each sample discharge line (43) having a distinct sample discharge control valve (43*a*) disposed thereon;

a controller C for controlling the sample supply control valve (42*a*) and the sample discharge control valve (43*a*);

a distinct drainage line (50) connected to each sample supply line (42) of the sample supply and discharge unit (40) to supply the sample in real time to each sample bottle 30 and each distinct drainage line 50 having a drainage control valve (51) disposed thereon; and distinct sample supply quantity control line (60) connected to a sample supply quantity control portion (34) of each sample bottle to control the quantity of sample and each distinct sample supply quantity control line 60 having a distinct sample supply quantity control valve (61) disposed thereon.

2. The real-time automatic analysis system according to claim 1, wherein the heating block (20) further comprises an agitator (24) adapted to agitate the sample of the accommodation portion (31) of each sample bottle (30) seated in the corresponding sample bottle seating recess (21).

3. The real-time automatic analysis system according to claim 1, wherein the distinct sample supply lines (42) of the sample supply and discharge unit (40) connected to the sample supply portion (32) of each sample bottle (30) is connected on the opposite end thereof to a water treatment facility or analysis water inclusive of raw water or processed water and has a pump (42*b*) adapted to supply the sample to each sample bottle (30).

* * * * *